United States Patent [19]

Lococo

[11] 4,382,785
[45] May 10, 1983

[54] MULTIPLE INLET DENTAL IMPRESSION TRAY

[76] Inventor: Michael P. Lococo, 4927 Victoria Ave., Niagara Falls, Ontario, Canada, L2E 1X1

[21] Appl. No.: 346,140

[22] Filed: Feb. 5, 1982

[51] Int. Cl.³ .............................................. A61C 9/00
[52] U.S. Cl. ...................................... 433/36; 433/37
[58] Field of Search .................................. 433/36, 37

[56] References Cited

U.S. PATENT DOCUMENTS

| | | |
|---|---|---|
| 2,155,334 | 4/1939 | Sitkin et al. |
| 2,349,607 | 5/1944 | Berger |
| 2,428,773 | 10/1947 | Beresin et al. |
| 2,452,903 | 11/1948 | Coffey |
| 2,458,145 | 1/1949 | Coffey |
| 3,304,608 | 2/1967 | Frohnecke |
| 3,357,104 | 12/1967 | Greene et al. |
| 3,722,097 | 3/1973 | Colman et al. |
| 4,080,736 | 3/1978 | Kennedy ............................ 433/36 |

FOREIGN PATENT DOCUMENTS

| | | |
|---|---|---|
| 417485 | 12/1943 | Canada . |
| 1007078 | 3/1977 | Canada . |

Primary Examiner—Robert Peshock
Attorney, Agent, or Firm—Stevens, Davis, Miller & Mosher

[57] ABSTRACT

A disposable dental impression tray is provided in its bottom with a number of inlets for injection of the impression material, preferably one inlet at each tooth. Each inlet has a connecting member, preferably defining a conical opening snugly receiving a tubular nip at the discharge end of a syringe. The syringe can thus be removably applied at any selected inlet of the tray to substantially reduce the pressure required for an accurate impression of the required area, as compared with known impression trays having only a single opening for injecting the impression material to obtain impression of several teeth, which often produces relatively poor impressions of the teeth remote from the opening. The readily detachable connection between the syringe and the tray provides for quick and convenient selective injection at the desired location. The tray is preferably produced from a generally transparent plastic material by injection molding and can thus be made as a disposable element.

8 Claims, 2 Drawing Figures

MULTIPLE INLET DENTAL IMPRESSION TRAY

The present invention relates to dental impression trays and in particular to dental impression trays of the type utilizing a syringe mechanism or the like for increasing the pressure at which the impression material is forced into the tray.

As mentioned in my copending Canadian patent application Ser. No. 381,626, filed July 13, 1981, the process of taking a dental impression includes the steps of preparing an impression mixture, usually a fairly fast hardening mixture, which is then placed into a tray, and if the tray is provided with a syringe, the syringe. The tray is then pressed to the desired area, usually having a soft rubber or the like seal around its edge, to provide at least a partial seal against the tissue about the rim of the tray. The impression material is then forced into the cavity of the tray, allowed to harden and then removed.

Prior art of the above type of impression trays is represented, for instance, by Canadian Pat. No. 417,485, issued Dec. 28, 1943 to Conway et al.; in Canadian Pat. No. 1,007,078, issued Mar. 22, 1977 to Lopez et al.; U.S. Pat. No. 2,155,334, issued Apr. 18, 1939 to Sitkin et al.; U.S. Pat. No. 2,349,607, issued May 23, 1944 to H. R. Berger; U.S. Pat. No. 2,428,773, issued Oct. 14, 1947 to Beresin et al.; U.S. Pat No. 2,452,903, issued Nov. 2, 1948 to Coffey; U.S. Pat. No. 2,458,145, issued Jan. 4, 1949, to E. G. Coffey; and U.S. Pat. No. 3,722,097, issued Mar. 27, 1973, to Colman et al, all of the foregoing prior art references being typical of different attempts made by artisans in order to improve the dental impression tray of the type mentioned at the outset.

To the best of the knowledge of the present applicant, the invensive efforts represented in the above prior art did not result in general acceptance of a dental impression tray utilizing a syringe. It is believed that the first commercially acceptable development of such impression tray is presented by the invention of the present applicant described in the above copending Canadian patent application. As mentioned in my previous patent application, the procedure accepted nowadays, is that a first, relatively thick or heavy bodied impression mixture is placed into a tray, whereupon the tray is pressed against the tissues surrounding the area whose impression is eventually to be obtained. Upon hardening of the relatively thick impression material, a reasonably accurate impression of the soft tissue is obtained. Then, the impression material is cut out of the bottom section of the impression tray, leaving only a relatively narrow margin around the edge of the tray. The tray is then filled in with a relatively thin or light bodied impression material and pressed again to the same area. The first impression aids in preventing free escape of the thin impression material from within the tray as the tray is subjected to pressure, thus assisting in providing the impression of the tooth.

The accuracy of an impression provided by the above method was substantially improved by my previous invention which also provides substantial simplification of the cleaning of the syringe.

It has now been discovered that there is room for a further improvement of the syringe equipped impression tray. In particular, it was found that if an impression tray is used to produce impression of a number, say four, teeth, then the impression by the injected light bodied material at a location relatively remote from a single inlet into the tray for the light bodied material is not as accurate as that in the immediate vicinity of such inlet. Furthermore, even the substantially simplified impression tray of my previous invention appears to be still too complex for convenient cleaning.

It is an object of the present invention to provide further improvement in the art of impression trays of the above type.

In general terms, the present invention provides, in one aspect thereof, a dental impression tray comprising: a concavely shaped inner part defined by a bottom wall and by a plurality of side walls and having the shape of an arcuately elongated cavity for receiving an impression material; a plurality of passages in said bottom wall, said passages communicating said cavity with the exterior of the tray, said passages being arranged along a curve following the arc of said arcuately elongated cavity and being spaced a predetermined spacing from each other; connecting means at an exterior of said bottom wall and near each passage for releasably connecting the respective passage to an outlet of injection means for injecting a pasty impression material into said tray; whereby a pasty impression material can be injected into said cavity at at least two discrete locations spaced from each other along the cavity.

The invention can also be defined in general terms as providing, for use with a syringe for injecting a pasty impression material and including a cylindric barrel, a plunger axially movable within the barrel and a discharge passage for discharging the impression material in a direction radially away from the barrel, said discharge passage being in communication with a connecting member forming a part of said syringe: a dental impression tray, comprising: a concavely shaped inner part defined by a bottom wall and by side walls cooperating with the bottom wall to form an elongate cavity for receiving a pasty impression material; a number of discrete connecting elements disposed exteriorly along said bottom wall, each of said connecting elements being complementary with the connecting member of the syringe for detachable connection of the tray to the syringe; said connecting elements being each adapted to communicate the syringe with said cavity for injecting a pasty impression material into said cavity; whereby a pasty impression material can be injected into said cavity at at least two discrete locations spaced from each other along the cavity.

The invention will now be described by way of an exemplary embodiment with reference to the accompanying diagrammatic drawing wherein.

Figure 1:
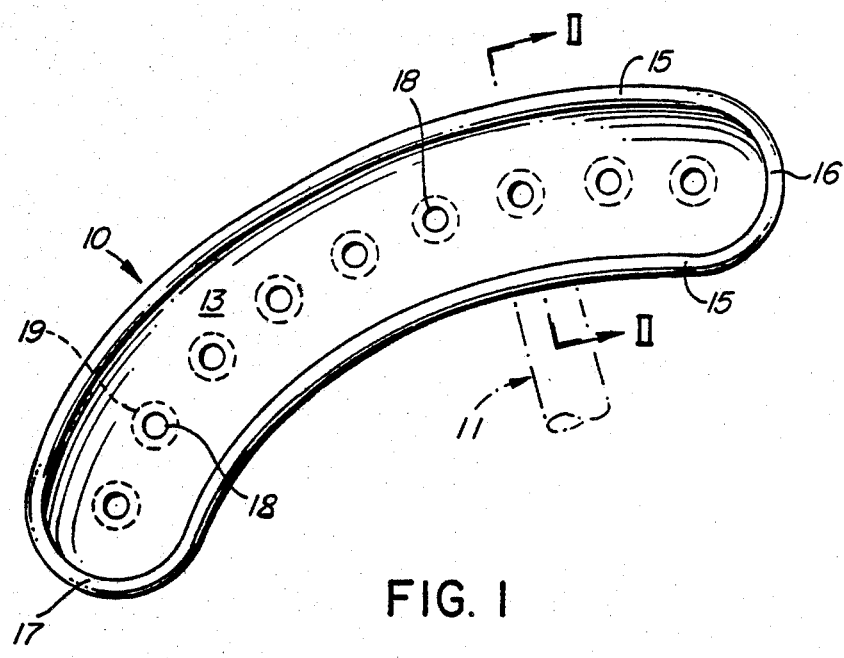
FIG. 1 is a top plan view of an impression tray according to the present invention.

It should be noted at the outset of the description of the exemplary embodiment that the drawing is not to scale and that many possible additional elements may be included in an actual product, such embodiments being omitted from the description for the sake of clarity.

Turning now to the embodiment shown in the drawings, the dental impression tray 10 is adapted to operate with a syringe 11. The tray shown in the drawing is made by injection molding from a suitable plastic material such as PVC which makes it possible to produce the tray in large quantities at a relatively low cost, thus making it possible to produce the tray as a disposable item. As is well known in the art, the tray 10 defines an arcuately shaped cavity 12 which is formed by a bottom wall 13 and by side walls 14, 15 which merge, at each end with the respective end wall 16, 17. For the sake of convenience, the side and end walls can be referred to by the same term of "a side wall". The side walls 14-17 thus cooperate with the bottom wall 13 to form an elongate arcuate cavity into which a relatively thick and fast hardening impression material of pasty consistency can be placed.

In the bottom wall 13 is provided a number of openings such as a port or passage 18. As best seen from FIG. 2, the opening 18 is disposed centrally of an outwardly directed annular protrusion or boss 19 in which is arranged a conical opening or passage 20 which is divergent in downward direction, that is in the direction away from the cavity 12. The medium diameter of the conical passage 20 is designed such that it roughly corresponds to the outer diameter of a nipple 21 at the end of a barrel 22 of the syringe 11. Within the barrel 22 is slidably received a piston or plunger 23 for expressing out of the interior of the barrel 22 the pasty impression material through the opening 24 in the nipple 21. It can thus be appreciated that the nipple 21 can be readily inserted into the conical passage 20 and with its free end portion engaged with the surface of the conical passage 20, a virtually sealed arrangement is achieved while at the same time allowing convenient and fast detachment of the syringe from the passage 20 and subsequent connection to any of the other remaining passages in the protrusions 19.

It was discovered that with the arrangement as described above, one can operate generally as described in my previous application, that is to say a relatively thick impression material is used first to provide preliminary impression, whereupon the impressed hardened material is drilled away from the tray such as to obtain space for the light bodied impression material through the desired one or more of the ports 18. The ports 18 are so spaced from each other that their spacing generally corresponds to the spacing of respective teeth in one half of a human jaw so that the respective ports 18 are in an immediate vicinity of the respective teeth the impression of which is to be obtained. Due to the immediate viscinity of the ports 18 to the respective teeth, it is thus possible to utilize a surprisingly low pressure in expressing the light bodied pasty material from the syringe 11 while achieving excellent results with respect to accuracy of the respective impression. Due to the simplicity of the overall structure of the impression tray, it can be produced as a disposable impression tray from a suitable plastic material, thus avoiding the need for cleaning of the tray after the desired impression or impressions have been taken.

Figure 2:
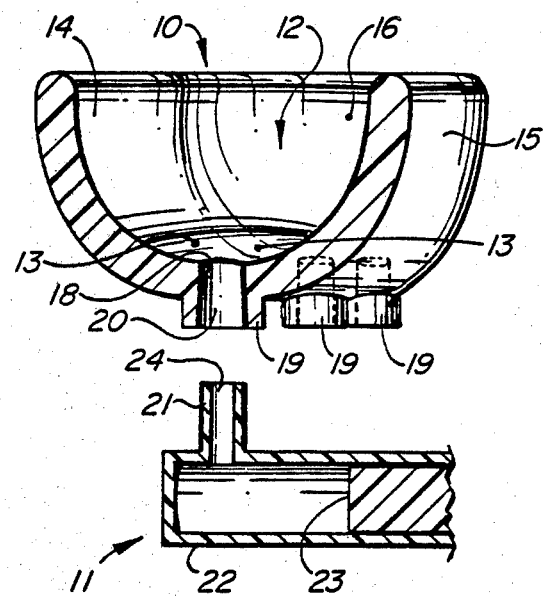
FIG. 2 is section II—II of FIG. 1, not to scale, and also including a diagrammatic representation of a syringe arranged for cooperation with the tray.

In operation, the tray of FIG. 2 is first filled with a relatively thick or heavy bodied impression mixture, and is then hand pressed against a selected portion of the upper jaw, with the orientation of the tray being reversed if the lower jaw is involved. The tray is then removed to obtain preliminary impressions of the respective teeth impressed in the thick material. Upon hardening, each part of the impression which is to be accurately reproduced is drilled off such as to provide a passage through the respective conical opening 20 and space for the injection of light bodied impression mixture. Then the tray is reapplied and light bodied impression material injected by the syringe 11 through the respective openings 20 of the bosses 19. At each respective tooth, the light bodied material completely fills in the cavity produced by the drilling off of the hardened heavy bodied material. It was found out that extremely low pressure at the syringe plunger 23 produces excellent results from the standpoint of accuracy of the impressions.

Those skilled in the art will readily appreciate that several modifications of the present invention may exist without departing from the scope of the present invention. For instance, while the provision of the connecting means of a cylindric nipple 21 and conical passage 20 is believed to be an optimum solution due to the simplicity of the shapes involved, this is not to say that other modifications may not be feasible. For instance, the free end portion of the nipple 21 of the syringe may be provided with an annular protrusion or seal to further improve the sealing engagement between the nipple 21 and the conical opening 20. The conical opening 20 may be produced on the syringe while the tray would be provided with functional counterparts of the nipple 21 as shown in FIG. 2. The number of the plurality of ports 18 and the associated bosses 19 is also optional and is preferably between 2 to 8. It is conceivable, however, that the number could be even greater than 8. Therefore, the invention is not limited to the number of ports 18 as shown in the drawings.

It is preferred that the tray be provided with the ports 18 at the time of production of the tray. This, however, does not necessarily suggest that the opening 26 and port 18 must be produced at the time of injection molding of the tray. For instance, an arrangement wherein the passage 20 and port 18 would be drilled during the removal of the heavy bodied material in combination with a modified releasable connection between the nipple 21 and the protrusion 19 is also possible.

It follows from the above that many further embodiments departing to a greater or lesser degree from the embodiment described above may exist without departing from the scope of the present invention as set forth in the accompanying claims.

The embodiments of the invention in which an exclusive property or privilege is claimed are defined as follows:

1. Dental impression tray comprising:
    a concavely shaped inner part defined by the bottom wall and by a plurality of side walls and having the shape of an arcuately elongated cavity of a width greater than the teeth upon which the tray is to be placed to define a space adjacent such teeth for receiving an impression material;
    a plurality of impression material injection passages communicating said cavity with the exterior of the tray, said passages being arranged along a curve following the arc of said arcuately elongated cavity and being spaced from each other a distance selected such that the spacing between the centers of two adjacent passages generally corresponds to the spacing between the centers of two adjacent teeth of a human jaw;
    connecting means at an exterior of said bottom wall and near each passage for releasably connecting each respective passage to an outlet of injection means for injecting a pasty impression material into said tray;
    whereby a pasty impression material can be injected into said cavity at at least two discrete locations spaced from each other along the cavity.

2. Dental impression tray as claimed in claim 1, wherein the connecting means of any of said passages is generally identical with the connecting means of any other passage of the tray to render each of the connecting means complementary with an outlet of a given injection means such as a syringe.

3. Dental impression tray as claimed in claim 1, wherein each connecting means is a hollow conical section communicating with the respective passage and divergent in a direction away from the respective passage, said hollow conical section being selected such as to be complementary with a tubular nipple at an outlet of a syringe for injecting a pasty impression material into the tray.

4. Dental impression tray as claimed in claim 1, wherein the number of said passages is 2 to 8.

5. For use with a syringe for injecting a pasty impression material and including a cylindric barrel, a plunger axially movable within the barrel and a discharge passage for discharging the impression material in a direction radially away from the barrel, said discharge passage being in communication with a connecting member forming a part of said syringe:

a dental impression tray, comprising:
(a) a concavely shaped inner part defined by a bottom wall and by side walls cooperating with the bottom wall to form an elongate cavity of a width greater than the teeth upon which the tray is to be placed to define a space adjacent such teeth for receiving a pasty impression material;
(b) a number of discrete connecting elements disposed exteriorly along said bottom wall, each of said connecting elements being omplementary with the connecting member of the syringe for detachable connection of the tray to the syringe, the spacing between the centers of each pair of adjacent connecting elements corresponding approximately to the spacing between the centers of a pair of adjacent teeth of a human jaw;
(c) said connecting elements being each adapted to communicate the syringe with said cavity for injecting a pasty impression material into said cavity;
whereby a pasty impression material can be injected into said cavity at at least two discrete locations spaced from each other along the cavity.

6. A dental impression tray as claimed in claim 5, wherein the number of said connection elements is 2 to 8.

7. A dental impression tray as claimed in claim 5, wherein said connecting element is a conical opening in the bottom wall of the tray, the opening converging in the direction towards the elongate cavity and having a diameter complementary with the connecting member of a respective syringe.

8. An impression tray as claimed in any of claims 5, 6 or 7 produced by molding from at least partially transparent material.

* * * * *